(12) United States Patent
Cardarelli

(10) Patent No.: US 6,532,598 B1
(45) Date of Patent: Mar. 18, 2003

(54) PATIENT MASK

(76) Inventor: Venanzio Cardarelli, 20 N. Triangle Dr., Plymouth, MA (US) 02360

( * ) Notice: Subject to any disclaimer, the term of this patent is extended or adjusted under 35 U.S.C. 154(b) by 0 days.

(21) Appl. No.: 10/072,279

(22) Filed: Feb. 7, 2002

(51) Int. Cl.$^7$ ................................................ A42B 1/18
(52) U.S. Cl. ....................... 2/173; 128/206.19; 128/858
(58) Field of Search ................ 2/9, 171, 173, 2/206, 410, 424, 426, 427, 428, 6.3; 128/206.19, 206.23, 201.15, 206.13, 201.29, 201.17, 206.12, 206.21, 201.12, 203.29, 201.24, 853, 857, 858; 433/136, 137, 138

(56) References Cited

U.S. PATENT DOCUMENTS

| | | | |
|---|---|---|---|
| 4,122,847 A | 10/1978 | Craig | 128/858 |
| 4,709,695 A | 12/1987 | Kohn et al. | 128/858 |
| 4,969,473 A | 11/1990 | Bothwell | 128/858 |
| 5,226,815 A | 7/1993 | Bowman | 128/853 |
| 5,558,089 A | 9/1996 | Castiglione | 128/203.09 |
| 5,596,985 A | 1/1997 | Collier | 128/201.29 |
| 5,682,879 A | 11/1997 | Bowers | 128/201.12 |
| 5,694,925 A | 12/1997 | Reese et al. | 128/206.19 |
| 5,937,445 A | 8/1999 | Ravo et al. | 128/201.24 |
| 6,079,980 A | 6/2000 | Durand | 128/206.13 |
| 6,185,740 B1 | 2/2001 | Zegarelli et al. | 128/206.19 |

*Primary Examiner*—Gary L. Welch
(74) *Attorney, Agent, or Firm*—D. Michael Burns

(57) ABSTRACT

A lightweight and inexpensive mask providing protection to the nose and eyes of dental patients from contaminants that are present in the dental office. The Mask having a nose portion having an elasticized cord transversing across the philtrum area of a patient thereby causing the mask to adopt a triangular shape about the nose. The nose portion being caused to create a natural ventilation along the nasolabial groove areas of the patient. The mask further including a pair of transparent eye panels and means for affixing the mask on the patient's face.

1 Claim, 4 Drawing Sheets

PATIENT MASK

BACKGROUND OF THE INVENTION

1. Field of the Invention

The present invention relates generally to a patient mask that is designed to be worn by dental patients, and more specifically to a mask that protects the eyes and nose of the patient.

2. Description of the Prior Art

The environment in a dental office can be detrimental to the health of both the patient and the dental staff. In addition to harmful aerosols, which studies have shown may contain up to 100,000 bacteria per cubic foot of air within three feet of the patient, the dental office may regularly contain nitrous gases, disinfectant fumes, mercury vapors, sterilization fumes, tooth dusts, fillings dust, sulfates, polyether fumes, viruses, saliva and blood droplets. The aerosols generated by air polishers are particularly harmful. High speed cutting instruments (200,000 to 300,000 rpm) generate considerable heat which can cause injury to the tooth pulp. To prevent this, water spray is employed as a coolant and a lubricant. As a result, there are microbial aerosols which are generated from the patient's mouth during dental procedures which are comparable in bacterial concentrations to those produced during coughing and sneezing.

Transmission of infection requires a series of factors: a source of reservoir for the pathogen, a pathogen of sufficient infectivity and number, a mode of escape from the host, and a portal of entry. Infection-control techniques seek to eliminate one or more links in the chain of infection. Barrier products such as masks are viewed as a means of protecting both patients and dental staff from pathogens in potentially infectious sprays, splash and splatter. The guidelines of O.S.H.A. are for the protection of employees, not the patient. The dentist sees that dental assistants, hygienists as well as himself/herself are somewhat safe. They wear safety glasses, shields, masks and gloves. But no one has been at the forefront with concern of the patient; aside from making sure that the instrumentation is properly sterilized to protect against cross contamination and infection. The patient is exposed to the same environment as is the dentist and staff. The cloud of bacteria within the two to three foot area of the patient is very susceptible to the patient because during dental procedures the "interior milieux" of the patient is disturbed. The breathing is mostly through the nose since the mouth is the work site. The nose of the patient needs a filter and the patient's eyes need to be shielded from flying debris. Sensitivities can develop into allergies, infected nasal passages, infected sinuses, irritated cilia, reflective sneezing and coughing. The patient must be protected from all of this. It is imperative that a patient mask be available that is lightweight, inexpensive, comfortable, and which will protect both the eyes and nose of the patient.

The prior art does have some masks designed to be used by the patient. One such mask was described in U.S. Pat. No. 4,969,473 issued to Bothwell on Nov. 13, 1990. This mask resembles a hood that one would use to cover virtually the entire head of the patient, both front and back. While it would certainly provide for the much needed protection for the patient, it would appear to be far more costly than necessary.

U.S. Pat. No. 4,122,847 issued to Craig on Oct. 31, 1978 is typical of the type of protection for the eyes of sugical patients. This patent does not protect the patient's nose which will be the primary portal for contamination into the patient's lungs.

None of the above inventions and Patents, taken either singly or in combination, is given to describe the instant invention as claimed.

SUMMARY OF THE INVENTION

Accordingly, the above problems and difficulties are obviated by the present invention which provides for a disposable mask designed exclusively for the patient, especially dental patients.

More particularly, the mask is made from very lightweight, inexpensive materials that will provide protection for the nasal passageway, yet not interfere with the visibility of the dentist performing an oral procedure. Many dental procedures create flying debris and the mask must also protect the patient's eyes.

The present invention will utilize a material quite similar to the disposable materials used as bibs and/or dental masks which utilize rigid to semi-rigid material as well as soft pleated material. The lightweight and inexpensiveness being important. It is suggested that the mask of the present invention be packaged along with the bib, perhaps even as one piece, whereby the mask can then be torn off fom the bib for use. The conventional ties that hold the masks to the user's head are an optional design as the present invention would utilize a dead soft material over the ridge of the nose to hold the mask in place. Since the patient is in a prone position, the soft metal strip would suffice in most applications. In this way the mask will not interfere with a patient's hairdo or cosmetic make-up.

The present invention is comprised of two areas of protection, which is presented as a one piece mask providing protection for the nose and eyes. In the present invention, the protection for the eyes is in the form of panel windows. The mask material being of a fan type design and the eye panels being of a saran, polyester or polyethylene type transparent material. The nasal protection would be of the same lightweight, soft and comfortable material as the rest of the mask but with a possibility of increasing the thickness of such for extra filtration. This is especially important in the nares area. This is why the philtrum cover can be bent to give the double layer of protection or simply protect the pre-nares area by resting on the philtrum.

The present invention will provide a means for venting exhaled breath on either side of the alar-nares area. The ventilation will be best at the nasolabial groove area. This is a naturally occuring groove which extends from the lateral border of the alar of the nose to the outer surfaces of the lips. The nasolabial groove is more prominent as the person ages, thereby increasing the exhale venting passageway. The nasolabial groove is a formation coinciding with the function of the levator labii superioris (which raises the upper lip), the levator labii superioris alaeque nasi (which dilates the nares) and the zygomaticus minor muscle. The ventilation will be best at the nasolabial groove area at the ridge of the nose. The venting is important to allieviate the panic and increased frequency of breathing that accompanies a mask that is too confining.

An important object of the present invention is to provide protection to the patient from contaminants and flying debris during dental procedures.

Another object of the present invention is to provide a comfortable mask that will adapt to any size or shape face.

An object of the present invention is to provide a protective mask from the same lightweight and inexpensive materials from which disposable dental masks are made.

These and other objects will become readily apparent upon further review of the following specification and drawings.

DETAILED DESCRIPTION OF THE PREFERRED EMBODIMENT

Figure 1:
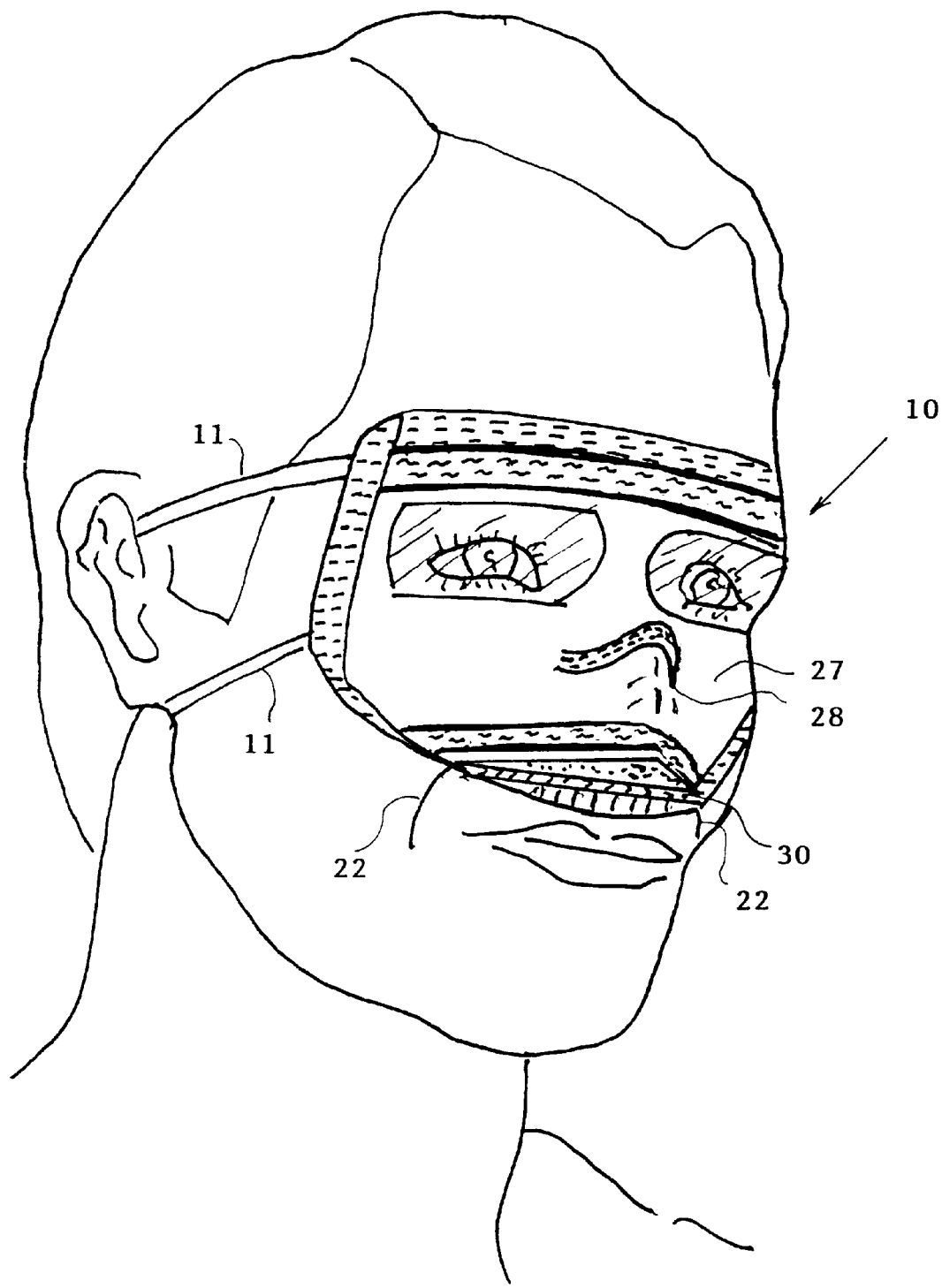
FIG. 1 is a perspective front view of the mask in accordance with the present invention disposed over the nose and mouth of a wearer.

Referring now to the drawings, FIGS. 1–4 illustrate a dental patient mask of the preferred embodiment. Like structure will be designated with like numerals throughout. FIG. 1 is a perspective view of the present invention, generally designated 10, installed to be worn over the nose and eyes of the dental patient. The mask 10 can be secured to the patient by a pair of tie strings 11 made of elastic material to provide a snug fit and the elasticity providing sufficient flexibility to allow single size ties to accommodate a range of head sizes. The mask 10 itself will be produced in various sizes to reliably fit a wide variety of individual faces. In FIG. 1 the tie strings 11 project about the patient's ears, but it is to be appreciated that other fastening means could work equally as well. In lieu of ties 11, the mask 10 can be adequately secured to the patient's head by means of a nose ridge strip. (to be discussed further)

Mask 10 is designed to protect the wearer from the flow of aerosols, viruses, bacterial, liquids, dusts and other airborne contaminants that are regularly found in dental offices. Aerosols are often by-products of microbial solutions and can be the most hazardous of all contaminants. The mask 10 is made of a fan design which allows the opening of it to accommodate the length of the face (eyes to nose) and the width of the nose. The mask 10 can be manufactured from a wide variety of lightweight, soft and comfortable materials. The first consideration in selecting an appropriate material is that it is imperative that the mask be disposable. The term disposable generally means that the cost of the mask is such that it may be disposed of after only a single use. The patient mask of the present invention will only be used a single time. While it may initially appear that disposing a mask after a single use increases the cost per use, such is often not the case. When the cost of preparing a reusable, pair of goggles (e.g. sterilizing the goggles) for reuse is considered, it is often less expensive to use a disposable mask/goggle combination which is designed to be sold for a few pennies.

The sheet of filter material, designated 26 in the figures, more particularly comprises a sandwich of materials which may be readily purchased in a pre-collated form, that is with two or three layers already bound together, or the materials may be obtained separately and the filter material formed as part of the process for forming the mask 10. Generally, a three layer filter medium might include, first, an outer facing layer of a relatively porous paper like material which provides durability such as that achieved with spun bonded polypropylene, which serves to slow down any liquid that may be splashed, sprayed of thrown at the mask 10. Often a layer of fluid impervious film may be disposed over the exterior surface of the filter sheet 26 to restrict moisture or vapor from penetrating. The second intermediate filter layer, such as melt blown polypropylene or polyester, serves to inhibit the passage of airborne bacteria in either direction, which will prevent passage of germs to and from the patient. And thirdly, an inner facing layer, which contacts the face of the patient, may be constructed of a lightweight, highly porous, softened, non-irritating, non-woven fabric, such as a spun bonded polypropylene, tissue or cellulous material.

Mask 10 is constructed so as to include a nose portion 12 and an eye portion 13. Eye portion 13 is basically made of pleated material, having an upper pleat 14 above the eyes and a lower pleat 15 below the eyes and over the dorsum-cartilagenous area of the nose for adapting the mask 10 to conform to various head shapes. The mask 10 includes exterior surface 27 and an interior surface (not expressly shown). Pleats 14 and 15 allow the mask 10 to bellow outwardly to easily conform to the general contour of the patient's face. Pleats 14 and 15 cooperate with one another to allow the mask 10 to expand and contract during normal breathing by the patient. Eye portion 13 having a pair of transparent eye panels 16 disposed therein between the outer and inner layers. The eye panels 16 being maintained therein by conventional heat sealing and/or sonic bonding techniques. The eye panel 16 material preferably comprises a clear plastic film such as that produced from saran, polyester, polyethylene, polycarbonate or any other lightweight inexpensive fluid impervious transparent material. The eye panels 16 protect the eyes of the patient from liquid spray and liquid splashes. Mask 10 having a frame 17 about the perimeter which would have an extra thickness of pleated material for comfort to the skin as well as adapting to form a seal with the face of the patient.

To enable nose portion 12 to be maintained in conformity with the shape of patient's nose, a malleable nose piece 18 is provided, shown in phantom since it is hidden by an overlying piece of retaining strip material 28, which may be spun-bonded polypropylene. The retaining strip 28 is attached to the underlying sheet of filter material 26, such as by ultrasonic bonding. Nose piece 18 can be manufactured of a soft elongated strip of malleable metal or moldable material longitudinally contoured therein for forming a tight seal between mask 10 and the patient's face. Suitable for use as a malleable metal would be a strip of aluminum, a thin gauge steel or even plastic having a cloth overlay. As previously discussed, the nose piece 18 would be adequate to maintain mask 10 in position without the need for the use of ties 11. As an added measure of adapting the mask 10 to the face an elongated sealing strip 19 comprising an aluminum strip is encapsulated within the top section 20 of the eye portion 13 by a binding of heat activated tape which is well known in the art and is commercially available.

The naso-philtrum area of the nose has an embedded elastic cord 21 which is circular or flat in cross-section for comfort to the patient and along with a malleable triangular shaping piece 31, shown in phantom since it is embedded in the lower pleat 15, giving it a somewhat rigid construction, and allowing the creation of a triangular geometrical configuration which is actually the key concept of the present invention. Elastic cord 21 extends from one nasolabial groove area 22 to the other, transversing across the naso-philtrum line 30 of the patient. Further the elastic cord 21 connects with the more rigid material of the lower pleat 15 to maintain the functional integrity of the mask 10. Further when mask 10 is placed over the face and nose of the patient, the elastic cord 21 will adapt so as to form a seal at the naso-philtrum line 30, and its constriction will accentuate the triangular chamber 29 and this will allow the mask 10 to enhance the natural venting along the nasolabial groove 22. A shaped infranasal fitration band 23 having a reinforced layer of filtering material is connected to the mask 10 along the naso-philtrum crease line 24. To protect the nares area of the patient as shown in FIGS. 1 to 4, the infranasal filtration band 23 is placed in a juxtaposed position against the nares openings, thereby preventing unwanted contaminants from entering the patient's respiratory system. Extending downwardly from the infranasal filtration band 23 is a philtrum cover 25 which provides protection for the patient's philtrum as well helping to create a seal so that contaminants do not move towards the patient's nares. Philtrum cover 25, is filtering material as well and it provides another important function in that it can be tucked underneath the infranasal filtration band 23. This provides an extra thick layer of filtration if it is required. The philtrum cover 25, if it interferes with any dental procedure may be moved by simply cutting it off. The shape of the nose portion 12 when the infranasal filtration band 23 is in place provides for a slight triangular geometrical configuration. A configuration which can be accentuated by the pull of the elastic cord 21 on the malleable triangular shaping piece 31 at the nasolabial groove area 22. This configuration tends to eliminate the claustrophobic feeling that occasionally occurs when the patient draws a breath, whereby the mask 10 is sucked into the face.

Figure 2:
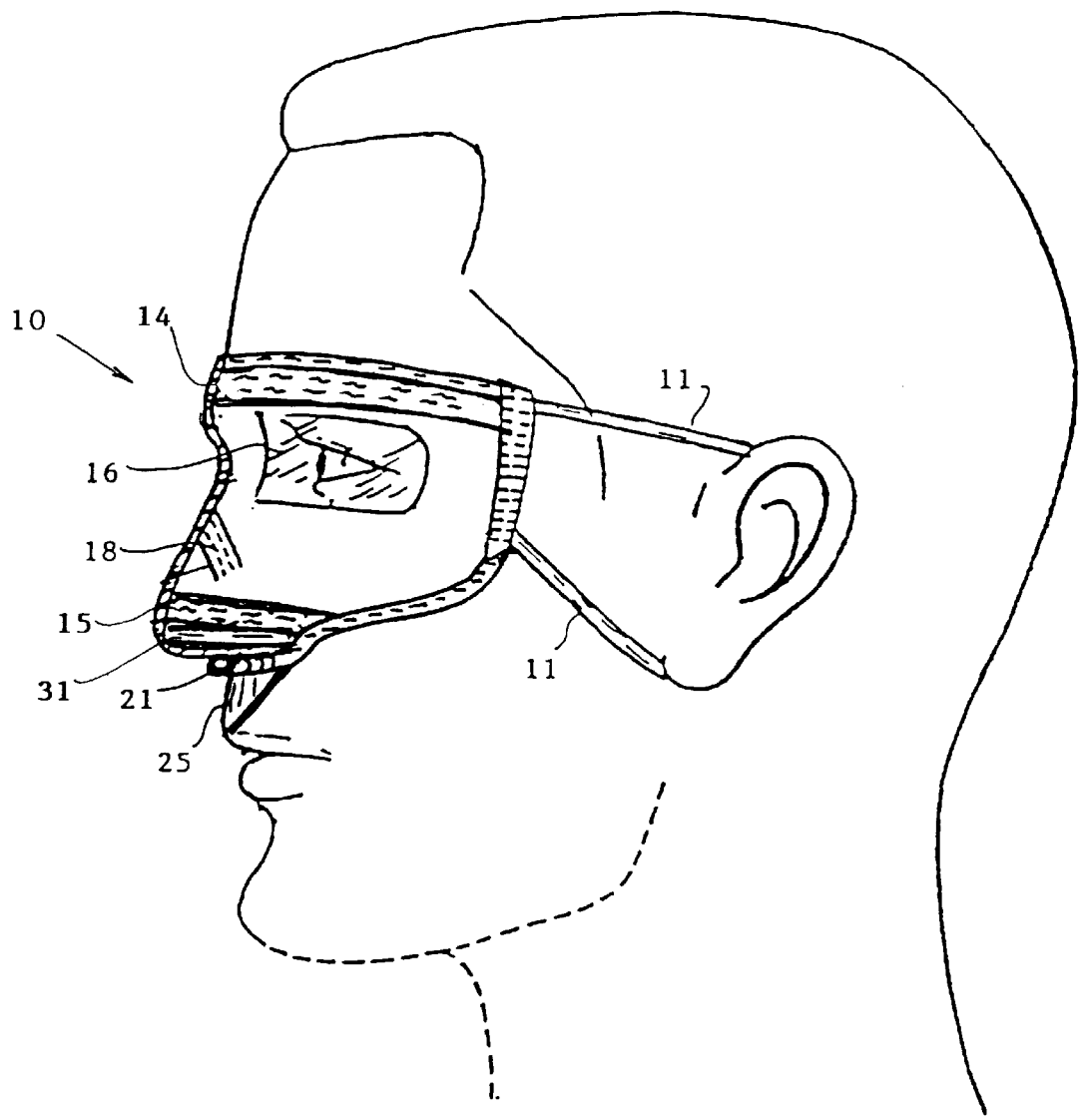
FIG. 2 illustrates a side view of the mask of the present invention.
Figure 3:
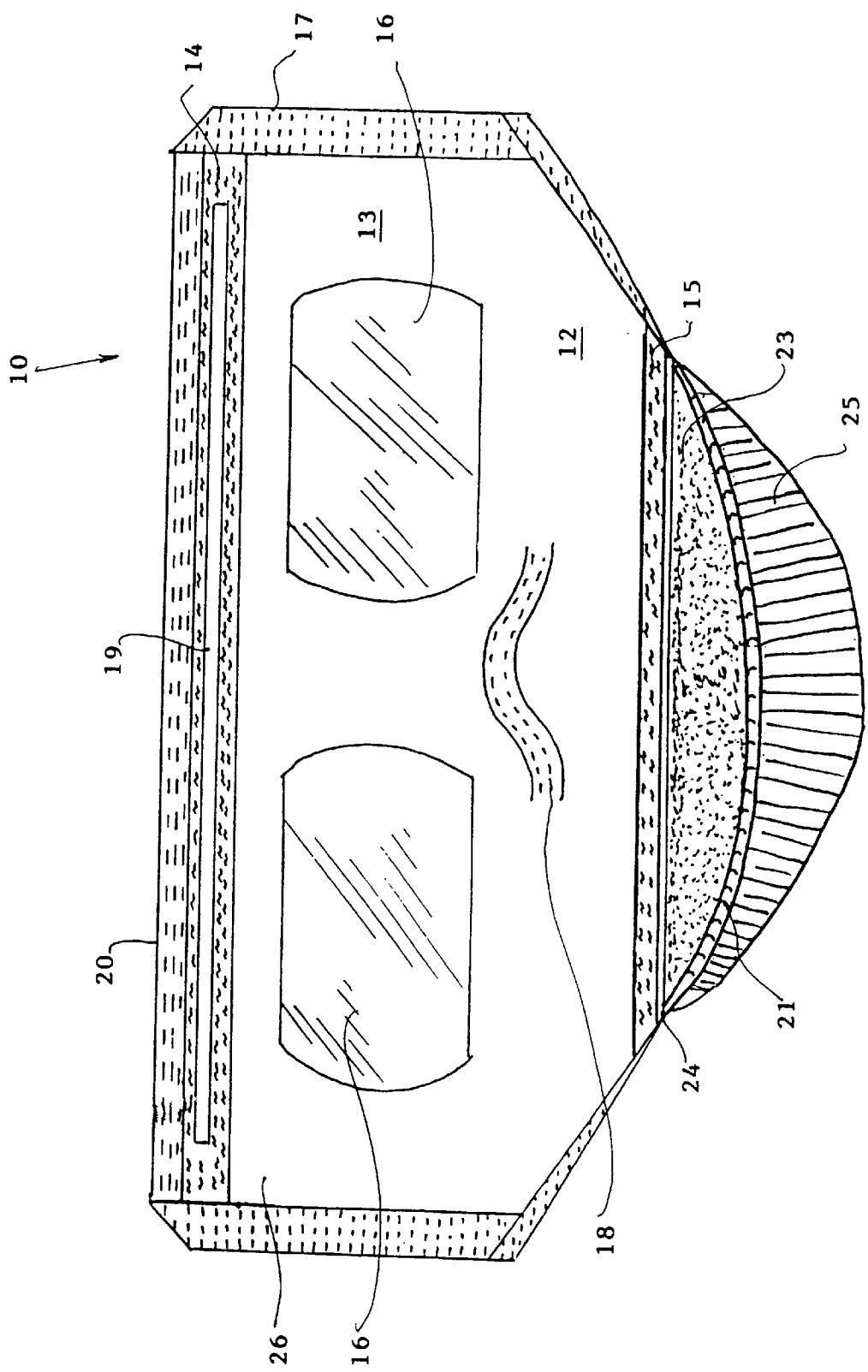
FIG. 3 is a front view of the mask of the present invention.
Figure 4:
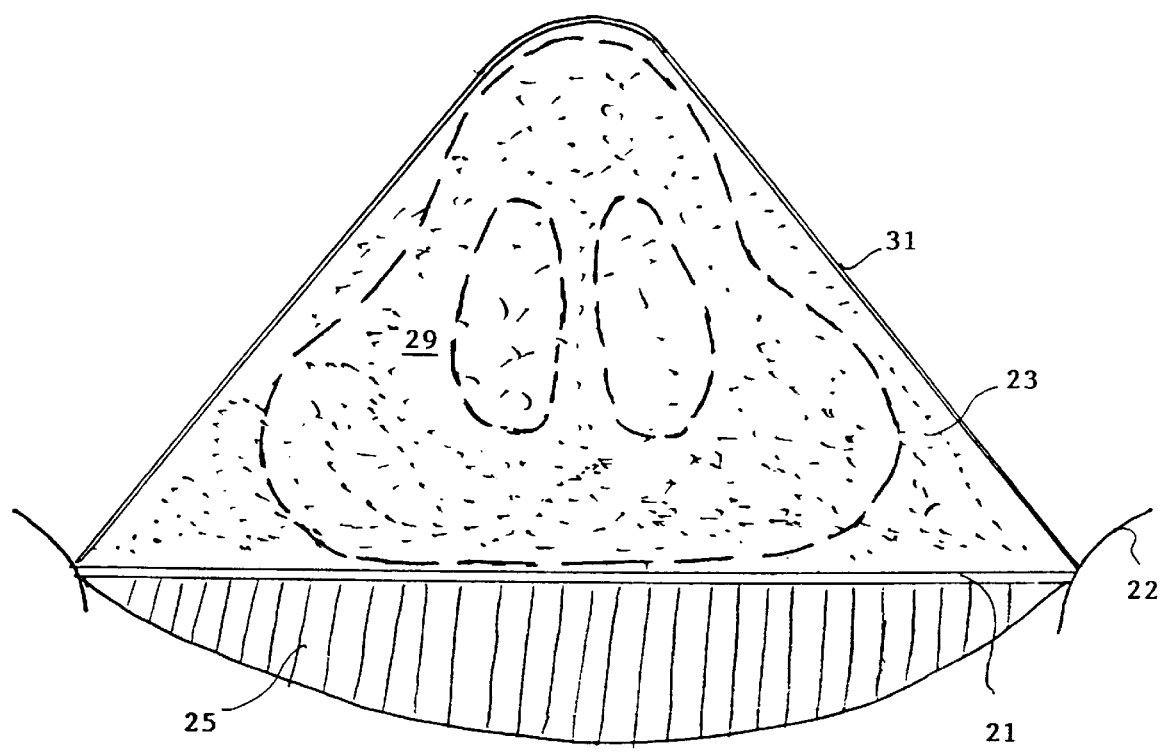
FIG. 4 is a view of the infranasal filtration band as it is juxtaposed across the naris area of the patient.

As represented in FIG. 3 the body of the mask has an essentially flat configuration for ease of packaging and storage. When opened for use as shown in FIGS. 1 and 2, the nose portion 12 forms a triangular geometric configuration. The primary goal of the present invention is to provide protection for the patient's eyes and nose during a dental procedure. This is done herein by providing the patient with an extremely simple, lightweight and inexpensive mask. The estimated cost of such a mask is but a few pennies and would be only a fraction of the cost of disposable goggles that are now being used.

While there has been described what is presently considered the preferred embodiment of the invention, it will be apparent to those skilled in the art that modifications and changes can be made therein without departing from the scope of the present invention as defined by the appended claims.

I claim:
1. A mask for a dental patient, the mask comprising:
an upper eye portion including:
   a pair of transparent eye panels,
   filtration material having an upper pleat conforming to the patient's face, the upper pleat dispersed above the eye panels; and
a lower nose portion integral with bottom section of the upper eye portion, the lower nose portion comprising:
   an elongated infranasal filtration band folded along a nasal philtrum crease line,
   an elastic cord embedded above the lower nose portion in cooperation with a malleable triangular shaping piece to form a triangular configuration extending between nasolabial groove areas of the patient to seal the mask on the patient's nasophiltrum line and creating natural ventilation along the nasolabial grooves,
   the nose portion including a lower pleat transposed over and conforming to the dorsum cartilagenous area of the patient's nose,
   an elongated philtrum cover extending downwardly from and folding under the infranasal filtration band to create an extra thick measure of filtration over the nares; and
means for securing the mask to the patient.

* * * * *